US00PP08854P

United States Patent [19]

Fruehwirth

[11] Patent Number: Plant 8,854

[45] Date of Patent: Aug. 2, 1994

[54] POINSETTIA PLANT '585'

[75] Inventor: Franz Fruehwirth, Encinitas, Calif.

[73] Assignee: Paul Ecke Ranch, Encinitas, Calif.

[21] Appl. No.: 162,991

[22] Filed: Dec. 7, 1993

[51] Int. Cl.[5] ..... A01H 5/00
[52] U.S. Cl. ..... Plt./86.2
[58] Field of Search ..... Plt. 86.2

*Primary Examiner*—James R. Feyrer
*Attorney, Agent, or Firm*—Arnold, White & Durkee

[57] ABSTRACT

Poinsettia '585' is a new cultivar the "curly" flower type, distinguished by creamy white flower bracts, unique flower bract formation and presentation, dark green foliage and self-branching characteristics. The new plant produces a very desirable branched flowering pot plant. The post-production foliage and bract retention is excellent even under low light intensities in the consumer's home.

1 Drawing Sheet

BACKGROUND OF THE NEW PLANT

This new poinsettia cultivar, '585,' originated as an induced self-branching sport of a seeding known as 'H-44' (proprietary) in my greenhouse in Encinitas, Calif. It was selected because of its unusual flower bract formation and bract presentation, white flower bracts, dark green foliage and self branching characteristics; traits which distinguish it from other poinsettia cultivars, and seem to make it a desirable plant for commercial green house production. After selection, '585' was vegetatively reproduced from stem cuttings for test purposes in Encinitas, Calif. By subjecting clones of this plant to successive generations of vegetative propagation, it was demonstrated that the distinctive characteristics of '585' held true from generation to generation.

DESCRIPTION OF THE PHOTOGRAPHS

Poinsettia '585' is illustrated in the accompanying color photographs.

The upper photo is a side view of 3 single stem plants per pot in full flower. Evidence of self-branching can be seen in the flowering auxillary branches beneath the upper canopy of bracts.

The lower photo is a top view of the same plants showing flower and bract formation.

DESCRIPTION OF THE PLANT

The following is a detailed description of this new poinsettia as observed in Encinitas, Calif., U.S.A. during December 1992. Observations were recorded from flowering plants, grown as 3 single stem plants per pot. The pot was 14 cm in diameter and 11 cm in height. Color designations are compared to the 1986 edition of R.H.S. Colour Chart, first published in 1966 by the Royal Horticultural Society, London, England.

This new plant of the "curly" flower type is distinctly different than the poinsettia named 'White Curly' (U.S. Plant Pat. No. 4,951) in the following respects. Poinsettia '585' is self branching; 'White Curly' has little tendency to branch. The stem stiffness of this invention is significantly improved over 'White Curly.' The bract color of '585' is a creamy white near RHS 2D; the bract color of 'White Curly' is yellowish white RHS 160C.

THE PLANT

Origin: Sport of a non-patented and undistributed seedling known as 'H-44.' The sport was induced by application of the procedures set forth in U.S. Pat. No. 4,724,276 herein incorporated by reference to the seedling plant. The rootstock used to create '585' was Dark Red Hegg (U.S. Plant Pat. No. 3,160).

Classification:

*Botanic.*—*Euphorbia pulcherrima* Willd.
*Common name.*—Poinsettia.
*Cultivar name.*—'585'.

Form: Shrub.

Height: Medium.

Growth habit: As a single stemmed plant, upright and vigorous with self-branching side shoots. The application of a chemical growth retardant may not be needed to restrict height for commercial pot plant production. I observed 3 unpinched plants in a pot with an overall height of 42 cm an an overall width of 36 cm. The bract diameter of individual flowers was 18 cm.

Branching: Axillary branches will develop and terminate in a flower without pinching. However, it is usually desirable to pinch '585' before flower induction and remove all terminal dominance. Then, all axillary branches will develop uniformly and at a faster rate.

Growth rate: Rooting of stem cuttings occurs in 12–18 days under intermittent mist. The plant will flower in about nine weeks under continuous long night conditions and night temperatures of about 16°–18° C.

Foliage: The foliage is clean and uniformly dark green from bottom to top of the plant. The leaves are of medium size, leaf blades typically being 8–9 cm long and 8–9 cm wide with leaf petioles 2–3 cm long.

*Leaf shape.*—Typical leaves are generally ovate with obtuse bases and acuminate tips. Leaf margins are both lobed and serrated with 1 or 2 indentations on each side of the leaf blade. The midrib is convoluted or curled and often twisted to the right. The unique appearance of the leaves may be described as puckered and arched as might be caused by pulling a drawstring inside the midrib.

*Color.*—Upper side — Dark green, near RHS 147A. Under side — Green, between RHS 147B–C.

*Retention.*—The foliage lasts extremely well even under low light intensities in the consumer's home.

Bracts: Generally there are 18–21 creamy white bracts of various sizes subtending the cyathia. The primary bracts have blades typically 8–9 cm long and 8–9 cm wide with petioles 1–2 cm long. The bract surface is rugose with the midrib convoluted or curled and often twisted to the right. Together, the convexity of the bracts make a coarsely convoluted, spherical flower head. The twisted bract tips form a counter-clockwise swirl when viewing the flowers from above.

*Shape.*—Primary bracts are ovate to elliptic with obtuse bases and acuminate tips. Primary bract margins are lobed, generally with 2 indentations on either side of the bract. Secondary bracts are ovate to elliptic, of various sizes and have entire margins.

*Color.*—Upper side — Creamy white, near RHS 2D. Under side — near RHS 4D.

Flowers: Generally, 19–22 cyathia (flowers) are present when the plant was in full bloom. Each cyathium is about 7 mm long and 6 mm wide, green in color, and fringed with yellow at the distal end. One, but often two yellow nectar cups protrude from the side of each cyanthium and secrete nectar. The flower pedicel is also green and about 5 mm in length. The stamens protruding from the cyathia are white. The anthers are bifurcate; the pollen is yellow and copious. The stigmas are creamy white and trifurcate.

*Nectar exudate.*—Abundant.

*Seeds.*—Self-incompatible.

*Fertility.*—Not observed.

Post production: The leaf, cyathium and bract retention is excellent and the bracts do not fade or discolor.

What is claimed is:

1. A new and distinct Poinsettia cultivar, substantially as herein shown and described, distinguished by its unusual bract formation and presentation, dark green foliage, and self-branching characteristics.

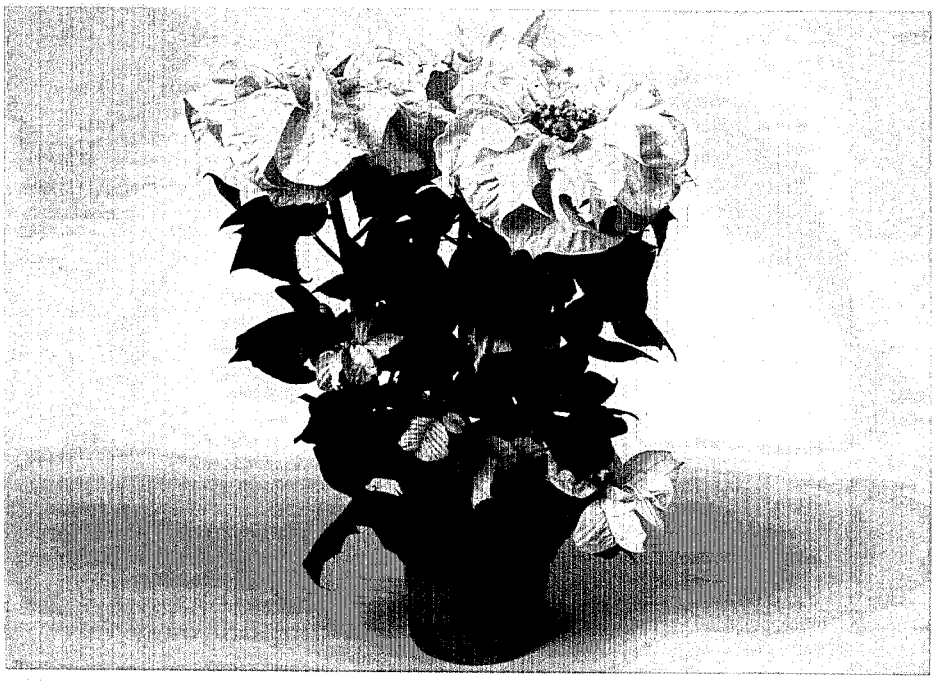
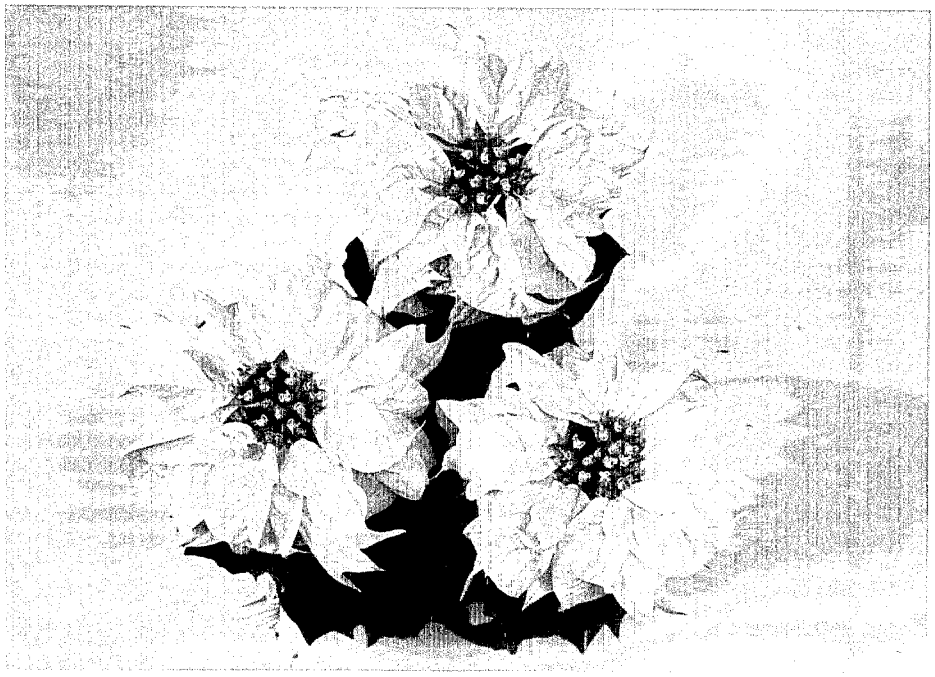

* * * * *